United States Patent
Bulger et al.

(10) Patent No.: US 8,715,952 B2
(45) Date of Patent: May 6, 2014

(54) ACETAMINOPHEN ASSAY

(75) Inventors: Michael Bulger, Price Edward Island (CA); Jan Holinsky, Valrico, FL (US)

(73) Assignee: Sekisui Diagnostics LLC, Lexington, MA (US)

( * ) Notice: Subject to any disclaimer, the term of this patent is extended or adjusted under 35 U.S.C. 154(b) by 0 days.

(21) Appl. No.: 13/544,477

(22) Filed: Jul. 9, 2012

(65) Prior Publication Data

US 2012/0301969 A1     Nov. 29, 2012

Related U.S. Application Data

(62) Division of application No. 12/425,482, filed on Apr. 17, 2009, now Pat. No. 8,236,519.

(60) Provisional application No. 61/048,406, filed on Apr. 28, 2008.

(51) Int. Cl.
    *C12Q 1/34*     (2006.01)
(52) U.S. Cl.
    USPC .......................................................... 435/18
(58) Field of Classification Search
    USPC .......................................................... 435/18
    See application file for complete search history.

(56) References Cited

U.S. PATENT DOCUMENTS

| 6,015,683 | A  | 1/2000 | Schaeffer et al. | 435/24 |
| 6,783,731 | B1 | 8/2004 | Arter et al. | 422/428 |

FOREIGN PATENT DOCUMENTS

| EP | 0750197 B1 | 4/2002 |
| JP | 3658621 B2 | 6/2005 |

OTHER PUBLICATIONS

Bertholf et al., "False-Positive Acetaminophen Results in a Hyperbilirubinemic Patient", Clin. Chem. 49:695-698 (2003).
Bulger et al., "Performance Characteristics of a Novel Acetaminophen Procedure Displaying Minimal Effects from N-Acetylcysteine (NAC) Interference", Annual Meeting of the American Association for Clinical Chemistry, San Diego, CA, Jul. 2007.
Mayer et al., "More on Interference of N-Acetylcysteine in Measurement of Acetaminophen", Clin. Chem. 44:892-893 (1998).
Polson et al., "False Positive Acetaminophen Concentrations in Patients with Liver Injury", Clin. Chim. Acta 391 :24-30 (2008).
Tyhach, "More on Interference of N-Acetylcysteine in Measurement of Acetaminophen", Clin. Chem. 45:584 (1999).
Afshari et al.., "Rapid Spectrophotometric Method for the Quantification of Acetaminophen in Serum". Anal Chim Acta 443:165-169 (2001).
Corbett, John. F., "Application of Oxidative Coupling Reactions to the Assay of p-Phenylenediamines and Phenols" Anal Chem 47(2):308-313 (1975).
Morris et al., "Development and Validation of an Automated Enzyme Assay for Paracetamol (acetaminophen)" Clin Chim Acta 187(2):95-104 (1990).
Chen et al., "Automated Spectrophotometric Assay for Urine p-Aminophenol by an Oxidative coupling Reaction", Ann Clin Lab Sci 34(3):336-340 (2004).
Hammond et al., "Development of an Enzyme-Based Assay for Acetaminophen", Anal Biochem 143:152-157 (1984).
Weeks et al., "The Pulse Radiolysis of Dearaled Aqueous Carbondale Solutions. I. Transient Optical Spectrum and Mechamism. II. pK for OH Radicals", J Phys Chem 70(7):2100-2106 (1966).
Vaughan P. et al., Amperometric Biosensor for the Rapid Determination of Acetamiophen in Whole Blood. Analytica Chimica Acta 248(2)363-365, 1991.
Walker M. et al., Performance Characteristics of a Novel Acetaminophen Procedure Displaying Minimal Effects From NAC Interference. Clinical Chemistry 53(6, Suppl) A92-3, 2007, presented Jul. 17, 2007.

*Primary Examiner* — Ralph Gitomer
(74) *Attorney, Agent, or Firm* — Sunstein Kann Murphy & Timbers LLP

(57) ABSTRACT

In general, the present invention provides a reliable assay for the quantitative determination of p-aminophenol in an aqueous sample. More particularly, the present invention provides a rapid enzyme-based assay for the quantitative determination of acetaminophen in a sample. The assay employs a xylenol chromophore and a catalyst that is preferably a weak oxidizer. The assay provides reliable results in the presence or absence of N-acetylcystiene (NAC) and can therefore be used to monitor acetaminophen levels during NAC treatment. Methods and kits for determining acetaminophen concentration in an aqueous sample are also provided.

23 Claims, 2 Drawing Sheets

ACETAMINOPHEN ASSAY

CROSS REFERENCE TO RELATED APPLICATIONS

This application is a division of U.S. patent application Ser. No. 12/425,482 filed Apr. 17, 2009, now U.S. Pat. No. 8,236,519, which claims benefit of U.S. Provisional Patent Application No. 61/048,406, filed Apr. 28, 2008, which is incorporated herein by reference.

FIELD OF THE INVENTION

In general, the present invention relates to an assay for determining the concentration of p-aminophenol present in a sample. More particularly, the present invention relates to an enzyme-based assay for determining the concentration of acetaminophen present in a sample.

BACKGROUND OF THE INVENTION

Drug toxicity is a leading cause of acute liver failure. In the evaluation of hepatic failure, the clinical laboratory plays a vital role in diagnosis so that appropriate treatment can be initiated in a timely manner.

Acetaminophen (N-acetyl-p-aminophenol) has long been prescribed as an analgesic and antipyretic. It is widely available without prescription and is an active component in many common therapeutic formulations, such as cold and flu remedies. The widespread use of this drug places it high on the list of suspected hepatotoxic agents in patients presenting with liver malfunction.

While therapeutic doses of acetaminophen rarely cause adverse effects, cases have been reported where chronic, excessive use of acetaminophen has led to hepatotoxicity and nephrotoxicity. Ingestion of acute overdose quantities of acetaminophen causes a depletion of glutathione stores and accumulation of toxic metabolites in the liver, which can cause severe or even fatal liver failure.

When acetaminophen is ingested in excessive quantities, a highly reactive intermediate, N-acetyl-p-benzoquinoneimine, accumulates in the liver. This intermediate reacts with thiols in the liver, particularly glutathione. Glutathione is oxidized to glutathione disulfide (GSSG). Excessive levels of GSSG in the liver cause necrosis. Acetaminophen toxicity is generally reported at serum concentrations above about 20 mg/dL (1324 µmol/L).

The glutathione precursor, N-acetylcysteine (NAC), is often administered as an antidote for acetaminophen overdose. About 70% of NAC administered is metabolized in the liver. It is believed that NAC functions as an antidote for at least the following reasons: it is a precursor for glutathione, it is a powerful anti-oxidant, and it increases the efficiency of GSSG reductase in the liver. The administration of NAC is believed to minimize or prevent the damage caused by an overdose of acetaminophen, at least in part, by replenishing glutathione stores and preventing an accumulation of GSSG in the liver.

A high concentration of NAC is often administered in an initial loading dose followed by maintenance levels of NAC throughout the course of treatment. The loading dose can result in serum levels of NAC of 2000 mg/L or higher, and maintenance levels are often about 800 mg/L to 1000 mg/L. It is desirable to monitor acetaminophen levels throughout the course of NAC treatment to ensure an appropriate therapeutic level is maintained while avoiding unnecessary or excessive exposure to NAC.

The incidence of accidental, as well as intentional, acetaminophen overdose has increased significantly. The diagnosis and treatment of acetaminophen overdose requires early detection and accurate measurement of the drug in the body. The amount of acetaminophen on board must be quickly and accurately determined so that clinicians can rapidly administer an appropriate therapeutic dose of NAC to the patient. There is a high demand for rapid, reliable and robust clinical assays for determining acetaminophen concentration in biological samples.

Known methods for determining acetaminophen levels in biological samples include, for example, various chromatographic and spectrophotometric techniques.

Gas-liquid chromatography and high-performance liquid chromatography have proven to be reliable and accurate methods for determining acetaminophen levels in biological samples, however both are lengthy procedures that require expensive instrumentation and a high level of technical skill to perform. Such methods are not particularly suited for Stat laboratories, where rapid results are required.

Differential spectrophotometry has been widely used but this method requires time-consuming solvent extractions, which are undesirable in clinical assays. More rapid spectrophotometric methods generally fail to offer the desired specificity.

Colorimetric techniques include simple colorimetty as well as enzyme-based colorimetric assays. Various immune-based assays are also available but these tend to be significantly more expensive and therefore less desirable, particularly in a clinical setting.

While enzyme-based assays are convenient and economical compared to immune-based assays, they are generally less reliable in that they are prone to interference with biological molecules often present in patient samples, such as bilirubin and hemoglobin. Elevated levels of such molecules in patient samples can cause false positive results (see, for example, Bertholf et al., 2003), which can potentially lead to misdiagnosis and inappropriate choice or dose of treatment.

Known enzymatic assays are also subject to interference in the presence of therapeutic levels of NAC. Therefore, enzymatic assays cannot generally be used to monitor acetaminophen levels during the course of NAC treatment due to inaccuracy in the acetaminophen levels measured. This is a significant disadvantage of known enzymatic acetaminophen assays.

Known enzymatic assays employ three main components: an aryl acylamidase enzyme, a chromogenic (or color-forming) compound, and an oxidizing agent of sufficient oxidative potential to catalyze the coupling reaction.

Aryl acylamidase cleaves the amide bond of acetaminophen to yield p-aminophenol and acetate. The p-aminophenol is then reacted with the chromogenic compound in an oxidative coupling reaction in the presence of an oxidizing catalyst to form a colored product. Typical catalysts include metal salts or metal complexes of species having reactive oxygen or functional groups, such as permanganate, periodate, persulfate, sulfate, or acetate. The change in absorbance, typically measured at a wavelength that captures the peak absorbance of the colored product, is then used to determine the concentration of acetaminophen in the sample. This may be determined by comparing the absorbance values obtained against a standard or set of standards having known acetaminophen concentration and assayed by the same method. The number of moles of colored product formed is typically proportional to the number of moles of acetaminophen initially present in the sample.

The earliest enzyme-based acetaminophen assays required very long incubation times, often greater than 1 hour for each of the hydrolysis and oxidative coupling reactions, thus rendering them unsuitable for use in an emergency clinical setting.

Hammond et al. (1984) developed a rapid enzyme-based assay for determining acetaminophen concentration in serum using an aryl acylamidase to hydrolyze acetaminophen to p-aminophenol. The p-aminophenol is subsequently reacted with o-cresol in an oxidative coupling reaction catalyzed by copper sulfate, to form an indophenol dye. The change in absorbance at the peak wavelength of the dye (615 nm) is then used to determine acetaminophen levels. While this method provides rapid detection of acetaminophen, it is subject to significant interference in the presence of therapeutic levels of NAC and cannot be used reliably during NAC treatment. A similar method utilizing o-cresol in the presence of an oxidizing catalyst is prone to bilirubin interference (Bertholf et al., 2003), leading to false positive results in hyperbilinibinemic patients.

Morris et al. (1990) disclose an automated enzyme-based assay for measuring acetaminophen in a sample. Automated assays are generally preferred for clinical laboratories. The method uses an aryl acylamidase for hydrolysis of acetaminophen to p-aminophenol, followed by oxidative coupling with 8-hydroxyquinoline in the presence of manganese ions to form a blue product. The reagents are lyophilized for storage stability and must be reconstituted prior to use. Assays involving a reconstitution step are less desirable than liquid-stable assays and are more prone to error.

Known acetaminophen assays using 8-hydroxyquinoline or a derivative thereof as a chromophore are subject to interference in the presence of therapeutic levels of NAC (i.e. >800 mg/L). The present inventors tested two commercially available acetaminophen assays (Genzyme Diagnostics P.E.I. Inc., PEI, Canada) containing either 8-hydroxyquinoline-5-sulfonic acid (8-HQ5SA) or 8-hydroxyquino line hemisulfate (8-HQHS) as the chromophore. Although accurate acetaminophen measurements in the absence of NAC were seen, there was a significant (i.e. >about 10%) decrease in acetaminophen recovery in the presence of therapeutic levels of NAC. It was discovered that the presence of NAC affected the oxidative coupling reaction in the assay rather than the enzymatic conversion of acetaminophen to p-aminophenol. There was a considerable difference in recovery between the 8-HQ5SA and 8-HQHS assays, with the 8-HQ5SA assay being significantly more susceptible to NAC interference, indicating that even a slight difference in the chemical structure of the chromophore can be crucial to the coupling reaction when NAC is present.

Chen et at (2004) describe an assay for quantifying p-aminophenol in urine to assess exposure to aniline in the workplace. Urine p-aminophenol levels serve as a biological marker of aniline toxicity since about 15 to 60% of absorbed aniline is oxidized to p-aminophenol in vivo. The urine must be acidified and pretreated to release free p-aminophenol from the conjugated forms excreted in urine. The assay involves an oxidative coupling reaction using 2,5-dimethylphenol (p-xylenol) as the chromophore to form a colored product. The coupling reaction is catalyzed by sodium periodate, a strong oxidizer, to form a colored product. It was speculated that quantifying p-aminophenol levels in urine may be useful for assessing acetaminophen overdose, although this was neither explored nor demonstrated.

Afshari and Lui (2001) describe a non-enzymatic method for quantification of acetaminophen in serum. Free unconjugated acetaminophen is first separated from endogenous interferents by an extraction step followed by hydrolysis to p-aminophenol using heat (i.e. boiling for 10 minutes) and acid. This is a non-selective hydrolysis reaction compared to an enzymatic reaction. The hydrolysis reaction is followed by oxidative coupling of p-aminophenol to 2,5-dimethylphenol (p-xylenol) in the presence of sodium periodate, a strong oxidizer, to form a colored product. The need to extract the acetaminophen from the sample and boil the samples renders this method undesirable for use in an emergency clinical setting and also unsuitable for automation.

While enzymatic acetaminophen assays are convenient and more affordable than immuno-based assays, many clinical laboratories favor the immuno-based assays since they are unaffected by the presence of NAC in a sample. It is desirable to reliably measure acetaminophen levels during the course of NAC treatment. Immuno-based assays are also less susceptible to interference in the presence of biological molecules, such as bilirubin and hemoglobin, often present in patient samples. Since serum levels of bilirubin and hemoglobin are not predictable from patient to patient, an assay that is prone to interference with these molecules will not provide a robust clinical test that is reliable for all patients.

It is therefore desirable to provide a rapid acetaminophen assay that is accurate and reliable in the presence or absence of NAC, and which is less expensive than conventional immuno-based assays. It is also desirable to provide such an assay which is also less susceptible to interference with biological molecules present in patient samples compared to known assays.

BRIEF DESCRIPTION OF THE DRAWINGS

Embodiments and of the invention will now be described, by way of example only, with reference to the attached Figures, wherein.

SUMMARY OF THE INVENTION

Figure 1:
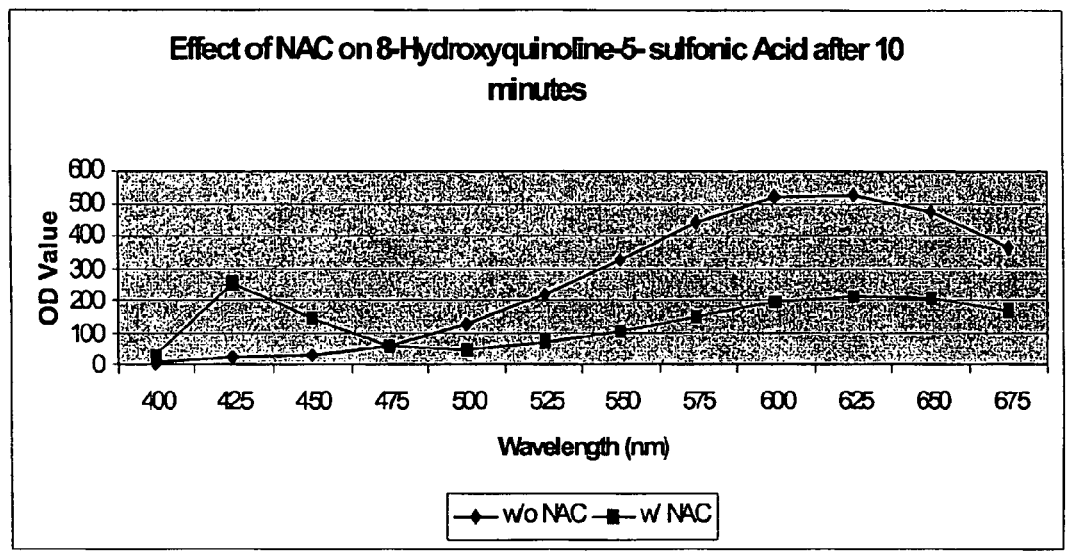
FIG. 1 shows the results of a prior art acetaminophen assay carried out in the presence or absence of therapeutic levels of NAC, with 8-hydroxyquinoline-5-sulfonic acid (8-HQ5SA) as the chromophore, wherein the results demonstrate that 8-HQ5SA shows significant interference in the presence of therapeutic levels of NAC.

In general, the present invention relates to a reliable assay for the quantitative determination of p-aminophenol in a sample. More particularly, the present invention relates to an enzyme-based assay for the quantitative determination of acetaminophen in a sample. The assay has an advantage over the prior art in that it provides accurate and reliable results in the presence or absence of NAC and can therefore be used to measure acetaminophen levels during NAC treatment. In certain embodiments, the assay has the additional advantage of improved performance and reduced interference with biological molecules compared to known assays.

It has been surprisingly discovered that the choice of a xylenol compound as a chromophore in an oxidative coupling reaction with p-aminophenol results in improved accuracy and reduced interference in the presence of NAC compared to other known chromophores.

In one aspect, the present invention provides a method for determining the concentration of acetaminophen in an aqueous sample. The method comprises the steps of hydrolyzing acetaminophen to p-aminophenol; oxidatively coupling the p-aminophenol to a xylenol chromophore in the presence of a suitable catalyst to form a colored product; and determining the amount of the colored product formed. The amount of the colored product formed is proportional to the amount acetaminophen initially present in the aqueous sample. The method is suitable for use in the presence or absence of therapeutic levels of N-acetylcysteine (NAC) in the aqueous sample.

In another aspect, the invention provides an assay for determining the concentration of acetaminophen in an aqueous sample, the assay comprising the steps of: contacting the aqueous sample with a first reagent (R1) comprising an aryl acylamidase enzyme and a suitable diluent to form a hydrolysis solution and optionally diluting the hydrolysis solution; incubating the hydrolysis solution to permit a hydrolysis reaction wherein the acetaminophen is converted to p-aminophenol; contacting the hydrolysis solution with a second reagent (R2) containing a xylenol chromophore and a suitable diluent to form an oxidative coupling solution; incubating the oxidative coupling solution to permit an oxidative coupling reaction wherein the xylenol chromophore is coupled to the p-aminophenol in the presence of a suitable catalyst to form a colored product; and determining the amount of the colored product formed, the amount of the colored product formed being proportional to the amount acetaminophen initially present in the aqueous sample, wherein the assay is suitable for use in the presence or absence of therapeutic levels of N-acetylcysteine (NAC) in the aqueous sample.

In another aspect, the invention provides a method for determining the concentration of acetaminophen in an aqueous sample, the method comprising the steps of: contacting the sample with an aryl acylamidase, resulting in the conversion of the acetaminophen in the sample into p-aminophenol; oxidatively coupling the p-aminophenol to a xylenol chromophore in the presence of a catalyst to form a dye; and determining the concentration of the dye, wherein the amount of acetaminophen in the original sample is proportional to the amount of the dye formed.

In another aspect, the invention provides a kit for determining the concentration of acetaminophen in a sample of blood, the kit comprising an aryl acylamidase, a xylenol, and a catalyst.

In another aspect, the invention provides a kit for determining the concentration of acetaminophen in an aqueous sample in the presence or absence of NAC, the kit comprising: a first vessel containing a first reagent (R1) comprising an aryl acylamidase for hydrolyzing acetaminophen to p-aminophenol; and a second vessel containing a second reagent (R2) comprising a xylenol chromophore for oxidative coupling to the p-aminophenol, wherein R1 or R2 further comprises a catalyst suitable for catalyzing the coupling of the xylenol chromophore to the p-aminophenol.

DETAILED DESCRIPTION OF THE INVENTION

In general, the present invention relates to a reliable assay for the quantitative determination of p-aminophenol in a sample. More particularly, the present invention relates to an enzyme-based assay for the quantitative determination of acetaminophen in a sample. The assay has an advantage over the prior art in that it provides accurate and reliable results in the presence or absence of NAC. In certain embodiments, the assay has the additional advantage of reduced interference with biological molecules compared to known assays.

The samples to be tested are preferably aqueous samples, meaning that they have an aqueous base component, Exemplary aqueous samples which may be tested in the assay include, but are not limited to, water, whole blood, plasma, serum, lymph, bile, urine, spinal fluid, sputum, saliva, perspiration, stool secretions, and the like. It is also possible to assay fluid preparations of human or animal tissue, such as skeletal muscle, heart, kidney, lung, brain, bone marrow, skin, and the like. Exemplary fluid preparations include tissue homogenates and supernatants thereof.

In one embodiment, the aqueous sample to be tested is plasma, serum, or urine. In another embodiment, the aqueous sample is plasma or serum. In one embodiment, the aqueous sample is serum.

While it is understood that the assay of the present invention may be carried out without the initial hydrolysis step, i.e. if p-aminophenol is to be measured directly in a sample, most typically the assay will be used to measure acetaminophen levels in a sample and will therefore require hydrolysis of acetaminophen to p-aminophenol prior to oxidative coupling of p-aminophenol with a selected chromophore. In accordance with the present invention, the selected chromophore is a xylenol chromophore. While a non-enzymatic hydrolysis reaction is possible, the preferred reaction is an enzymatic conversion of acetaminophen to p-aminophenol.

The assay of the present invention is typically carried out in two parts. The first part involves the enzymatic hydrolysis of acetaminophen to p-aminophenol. The second part involves the oxidative coupling of p-aminophenol to a xylenol chromophore in the presence of an appropriate catalyst to form a colored product. In some embodiments, the preferred catalyst is selected from weak oxidizers. The concentration of acetaminophen in the sample may then be determined, for instance, by measuring the change in absorbance at a given wavelength and comparing the value obtained against a standard or set of standards having a known acetaminophen concentration.

In one embodiment, the assay is a two-part assay carried out as follows.

In the first part, an aliquot of sample is brought into contact with a first reagent (R1) containing the enzyme to form a hydrolysis solution. This first reagent may be referred to as the enzyme reagent. The hydrolysis solution containing the sample in R1 is mixed and optionally diluted. In one embodiment, the optional dilution step involves a 1:1 dilution of R1 with a suitable diluent, such as deionized water. The solution is mixed and the hydrolysis reaction is continued to completion at an appropriate temperature to allow the hydrolysis of acetaminophen in the sample to p-aminophenol. An absorbance value is obtained at a given wavelength.

In the second part, upon completion of hydrolysis, a second reagent (R2) containing the xylenol chromophore is added to the hydrolysis solution and the resulting mixture is briefly mixed. The second reagent (R2) may be referred to as the chromophore reagent. Oxidative coupling of the xylenol chromophore with p-aminophenol requires the presence of a suitable catalyst. In one embodiment, the catalyst for the oxidative coupling reaction is a component of R1 such that the catalyst and chromophore do not associate until R1 and R2 are combined. Alternatively, the catalyst may be a component of R2, or may be added to the mixture of R1 and R2 to drive the oxidative coupling step. The oxidative coupling reaction is continued to completion at an appropriate temperature. Upon completion, absorbance is measured at a given wavelength and the change in absorbance between the first part and the second part is calculated.

To determine the amount of acetaminophen initially present in the sample, the change in absorbance is compared against a standard, or a set of standards, prepared by the same method and using known concentrations of acetaminophen. Dilution factors must be accounted for. Such calculations are routine to those skilled in the art.

This two-part assay is suitable for automation since no extraction or separation steps are required and only two reagents are utilized. On board dilution and mixing steps can also be carried out in an automated fashion. Automated instruments for carrying out such assays are well known in the art. Alternatively, the assay may be conducted manually.

The preferred enzyme for the hydrolysis reaction is an aryl acylamidase enzyme. Aryl acylamidase enzymes catalyze the hydrolysis of anilides to anilines, and are identified by the IUB (International Union of Biochemistry) number E.C.3.5.1.13. The CAS registry number for this class of enzymes is 9025-18-7. Aryl acylamidase enzymes are typically produced by and isolated from microorganisms, such as bacteria. Non-limiting examples of aryl acylamidase enzymes and methods of producing them from microorganisms are described, for example, in U.S. Pat. No. 4,430,433 to Hammond et al.

Any suitable aryl acylamidase enzyme may be used in accordance with the present invention so long as it is able to effectively catalyze the hydrolysis of acetaminophen to p-aminophenol under appropriate reaction conditions. The reaction conditions may be optimized by a person skilled in the art in view of the particular enzyme selected without departing from the present invention.

The aryl acylamidase may be present in any suitable amount. The aryl acylamidase is preferably present in a sufficient concentration such that substantially all of the acetaminophen present in a sample will be converted to p-aminophenol. In one embodiment, R1 comprises aryl acylamidase at a concentration of about 10 U/L to about 5000 U/L, or about 600 U/L to about 1200 U/L, or about 800 U/L to about 1000 U/L. In one embodiment, R1 comprises aryl acylamidase at a concentration of about 932.7 U/L.

The solvent or diluent for R1 may be any suitable aqueous-based solvent or diluent that does not negatively impact the assay. In one embodiment, the solvent or diluent is water, preferably distilled water, deionized water, or reverse osmosis water. In one embodiment, the diluent is deionized water. The solvent or diluent may comprise various additives and components.

In addition to the aryl acylamidase, R1 may further comprise one or more of a catalyst, a cofactor, a protein solubilizer, a protein stabilizer, an enzyme stabilizer, a metal chelator, a buffer, a surfactant, a pH adjuster, a preservative, a diluent, a solvent, an excipient or the like.

In one embodiment, R1 comprises the catalyst for the oxidative coupling reaction. Any suitable catalyst may be utilized in accordance with the invention, in any suitable concentration, if is capable of sufficiently catalyzing the oxidative coupling reaction. Exemplary catalysts include, but are not limited to, permanganates, periodates, persulfates, acetates, and other metal salts. In one embodiment, the catalyst is a metal salt selected from $FeCl_3$, $MnCl_2$, $CuSO_4$, $KIO_4$ or a derivative thereof. In a preferred embodiment, the catalyst is a weak oxidizer. In one embodiment, the weak oxidizing catalyst is manganese (II) chloride, $MnCl_2$. In one embodiment, the catalyst is manganese (II) chloride tetrahydrate, $MnCl_2.4H_2O$.

In certain embodiments, the catalyst is present in a concentration of about 0.0005 g/L to about 1.000 g/L, or about 0.005 g/L to about 1.000 g/L, or about 0.010 g/L to about 0.100 g/L, or about 0.025 g/L to about 0.075 g/L, or about 0.040 g/L to about 0.060 g/L. In one embodiment, R1 comprises $MnCl_2.4H_2O$ as a catalyst in a concentration of about 0.0525 g/L. The $MnCl_2.4H_2O$ may serve additional functions beyond its catalytic properties, for instance, it is believed that $MnCl_2.4H_2O$ may also act as an enzyme stabilizer to thereby improve the shelf-life of the enzyme reagent (R1).

In one embodiment, R1 comprises at least one protein stabilizer. A protein stabilizer will aid in the stabilization of the enzyme present in the reagent, thereby improving the shelf-life of the reagent. Any suitable protein stabilizer or combination thereof may be utilized in accordance with the invention.

One preferred protein stabilizer is PVP-40, which may also serve as a protein solubilizer in the reagent. The present inventors have found that PVP-40 can reduce or eliminate measurement errors in the assay caused by the presence of protein in the reagent and can prevent precipitation of protein in the reagent, thereby improving the shelf-life of the reagent and the overall performance of the assay. In one embodiment, R1 comprises PVP-40 in a concentration of about 0.1 g/L to about 10 g/L, or about 0.5 g/L to about 5 g/L, or about 1 g/L to about 3 g/L. In one embodiment, R1 comprises PVP-40 in a concentration of about 2 g/L.

In one embodiment, R1 comprises at least one protein stabilizer selected from PVP-40, BSA Fraction V, trehalose, sodium p-hydroxybenzoate, p-hydroxybenzoic acid or a combination thereof. In one embodiment, the at least one enzyme stabilizer comprises a combination of PVP-40, BSA Fraction V, trehalose and sodium p-hydroxybenzoate or p-hydroxybenzoic acid. The BSA Fraction V may be present in a concentration of, for example, about 0.1 g/L to about 10 g/L, or about 0.5 g/L to about 5 g/L, or about 1 g/L to about 2.5 g/L.

In one embodiment, R1 comprises BSA Fraction V in a concentration of about 1 g/L. Trehalose may be present in a concentration of, for example, about 0.1 g/L to about 10 g/L, or about 0.5 g/L to about 5 g/L, or about 1 g/L to about 2.5 g/L. In one embodiment, R1 comprises trehalose in a concentration of about 4.04 g/L. The p-hydroxybenzoic acid or p-hydroxybenzoic acid may be present in a concentration of, for example, about 0.1 g/L to about 10 g/L, or about 0.5 g/L to about 5 g/L, or about 1 g/L to about 2.5 g/L. In one embodiment, R1 comprises sodium p-hydroxybenzoate in a concentration of about 1 g/L. In one embodiment, R1 comprises p-hydroxybenzoic acid in a concentration of about 1 g/L.

In one embodiment, R1 comprises about 2 g/L PVP-40; about 1 g/L BSA Fraction V; about 4.04 g/L trehalose; and about 1 g/l sodium p-hydroxybenzoic acid.

R1 may optionally comprise a buffer. Any suitable buffer may be utilized in accordance with the invention. Suitable buffers may include, but are not limited to, phosphate, pyrophosphate, potassium phosphate, CAPS(N-Cyclohexyl-3-aminopropane sulfonic acid), CAPS/Metaborate, CAPS/Carbonate, tris(hydroxymethyl)aminomethane (TRIS), 2{[tris(hydroxymethyl)methyl]amino}-1-ethanesulfonic acid (TES), TRIS/Carbonate, 4-(2-hydroxyethyl)-1-piperazineethanesulfonic acid (HEPES), 3-[4-(2-hydroxyethyl)-1-piperazinyl]propanesulfonic acid (EPPES), 2-hydroxy-3-{N-[tris(hydroxymethyl)methyl]amino}-propanesulfonic acid (TAPSO), and combinations thereof.

The buffer may be present, for example, in a concentration of about 1 to 10 g/L or about 5 to 8 g/L. In one embodiment, R1 comprises CAPS buffer. In one embodiment, R1 comprises CAPS buffer in a concentration of about 6.4 g/L.

R1 may optionally comprise a preservative. Any suitable preservative may be utilized in accordance with the invention. Suitable preservatives include, but are not limited to, gentamycin sulfate, sodium azide, and sodium benzoate. In one embodiment, R1 comprises gentamycin sulfate in a concentration of about 0.001 g/L to about 0.1 g/L, or about 0.01 g/L to about 0.05 g/L. In one embodiment, R1 comprises about 0.01 g/L gentamycin sulfate. In one embodiment, R1 comprises sodium azide in a concentration of about 0.001 g/L to about 0.1 g/L, or about 0.01 g/L to about 0.05 g/L. In one embodiment, R1 comprises about 0.05 g/L sodium azide. In one embodiment, R1 comprises about 0.01 g/L gentamycin sulfate and about 0.05 g/L sodium azide.

R1 may optionally comprise a metal chelator. Any suitable metal chelator may be utilized in accordance with the invention. Suitable metal chelators include, but are not limited to, EDTA. In one embodiment, R1 comprises EDTA in a concentration of about 0.001 g/L to about 0.1 g/L, or about 0.01 g/L to about 0.05 g/L. In one embodiment, R1 comprises EDTA in a concentration of about 0.025 g/L.

R1 may optionally comprise a surfactant. Any suitable surfactant may be utilized in accordance with the invention. Exemplary surfactants include, but are not limited to, Brij™-35, Triton™ X-100, Olin-10G™, TX™-102, TX-405™, Zonyl FSN™, TX-100™, and TX-165™.

The hydrolysis reaction preferably takes place at a pH in the range of about 5.9 to about 12.0, or about 6.5 to about 9.0, or about 7.5 to about 9.4, preferably about 8 to 9. In one embodiment, the pH is about 8.6.

The pH of R1 may be adjusted by any suitable means known in the art. For example, NaOH or any other suitable base may be used to increase pH. HCl or any other suitable acid may be used to decrease pH. In one embodiment, the pH of R1 is adjusted using NaOH. In one embodiment, R1 comprises 2N NaOH in an amount of about 500 µL/L to about 1000 µL/L. In one embodiment, R1 comprises about 833 µL/L 2N NaOH.

An exemplary R1 formulation is provided in Table 1 below. In accordance with this exemplary embodiment, R1 may be prepared by adding each of the components, with the exception of the enzyme and sodium azide, to less than 100% total volume of a suitable diluent, preferably distilled water, deionized water or reverse osmosis water. The pH is then adjusted to the desired range with NaOH, followed by addition of the sodium azide. The enzyme is added last. The formulation is then made up to 100% volume with the diluent.

In one embodiment of an automated assay of the present invention, 10 µL of sample (or control or standard) is added to 100 µL of R1 in a cuvette. The R1 is then subjected to a 1:1 on board dilution with 100 µL water, preferably deionized water, distilled water or reverse osmosis water, and the solution is mixed briefly. The hydrolysis reaction takes place in the cuvette. Volumes may be adjusted depending on the size of the cuvette required for a particular automated instrument (i.e. chemical analyzer). In one embodiment, the chemical analyzer is a Hitachi 717® Chemical Analyzer (Roche Dignostics).

The hydrolysis reaction may take place at a temperature of about 10° C. to about 60° C., or about 30° C. to about 50° C., or about 35° C. to about 40° C. In one embodiment, the hydrolysis reaction takes place at a temperature of about 37° C.

The hydrolysis reaction is allowed to proceed for a sufficient amount of time to permit hydrolysis of substantially all of the acetaminophen present in the sample (or standard), typically between about 2 to 20 minutes or between about 3 to 10 minutes. In one embodiment, the hydrolysis reaction is continued for about 5 minutes. The length of the reaction can be optimized for the selected temperature since longer reaction times are generally needed for lower temperatures.

After the hydrolysis reaction is complete and substantially all of the acetaminophen in the sample (or standard) has been converted to p-aminophenol, the oxidative coupling step is carried out.

In one embodiment of an automated assay of the present invention, the oxidative coupling step is initiated by adding the second reagent (R2) containing the chromophore directly to the cuvette containing the hydrolysis solution. In accordance with the embodiment described above, 200 µL R2 is added to the hydrolysis solution, and is mixed briefly, for a final oxidative coupling reaction volume of 410 µL (10 µl sample+100 µL R1+100 µL water+200 µL R2) in the cuvette.

The accordance with the present invention, the preferred chromophore is a xylenol chromophore. The present inventors have surprisingly discovered that the choice of a xylenol chromophore in the present assay significantly reduced interference in the presence of NAC. This surprising result provides an advantage over prior art assays in that the present assay can be recommended for use during NAC treatment. The present inventors have shown reliable acetaminophen measurements in the presence of therapeutic levels of NAC up to at least 2000 mg/L, a result not previously demonstrated in any prior art enzymatic acetaminophen assay.

In an experiment, the present inventors also surprisingly found that replacing a 8-HQ5SA chromophore with 2,5-dimethylphenol in a commercially available acetaminophen assay (available from Genzyme Diagnostics P.E.I. Inc., PEI, Canada) resulted in significantly decreased bilirubin interference in the assay, further demonstrating that the choice of chromophore can significantly impact interference levels in the assay.

Any suitable xylenol chromophore may be utilized in accordance with the present invention, for example, 2,5-dimethylphenol, 3,4-dimethylphenol, 2,6-dimethylphenol, 2,4-dimethylphenol, 3,5-dimethylphenol or 2,3-dimethylphenol. Preferred xylenol chromophores result in minimal interference in the assay in the presence of therapeutic levels of NAC. In experiments, 2,5-dimethylphenol, 2,6-dimethylphenol or 2,3-dimethylphenol showed no significant interference with 1471 mg/L NAC in an interference assay. In one embodiment, the xylenol chromophore is 2,5-dimethylphenol (p-xylenol).

The xylenol chromophore may be present during the oxidative coupling reaction in any suitable concentration. In order to accurately calculate the acetaminophen concentration present in the initial sample however, the chromophore should ideally be present in a molar concentration that meets or exceeds the maximum p-aminophenol molar concentration in the hydrolysis solution, which is proportional to the amount of acetaminophen in the initial sample.

In one embodiment, R2 comprises the xylenol chromophore in a concentration of about 0.075 g/L to about 115 g/L, or about 2.5 g/L to about 20 g/L, or about 5 g/L to about 10 g/L. In one embodiment, the xylenol chromophore is 2,5-dimethylphenol and is present in R2 in a concentration of about 7.5 g/L.

In order for the oxidative coupling reaction to take place in a suitable timeframe, an appropriate catalyst must be present. The catalyst may be a component of R1 or R2, or may be added to the mixture of R1 and R2. A variety of catalysts can be used in accordance with the present invention, such as permanganates, periodates, persulfates, and various metal salts. In one embodiment, the catalyst is a metal salt, such as $FeCl_3$, $MnCl_2$, $CuSO_4$, or $KIO_4$. In one embodiment, the catalyst comprises anhydrous or hydrated $MnCl_2$. It was surprisingly found that $MnCl_2$, which is a weak oxidizer, was particularly effective in catalyzing the oxidative coupling step with p-xylenol compared to other metal salts tested.

Typically, for the oxidative coupling step in an acetaminophen assay, a catalyst having a strong oxidizing potential is selected to ensure enough energy is provided to drive the coupling reaction to completion. The catalysts generally employed are metal salts of species containing reactive oxygen or functional groups, such as sodium periodate, copper sulfate and manganese acetate. For instance, known acetaminophen assays have utilized hydroxyquinoline or its derivatives catalyzed by manganese acetate (i.e. Genzyme Diagnostics P.E.I. Inc., PEI, Canada); o-cresol catalyzed by periodate (GDS Diagnostics) or copper sulfate (Hammond et al., 1984); or p-xylenol catalyzed by sodium periodate (Afshari and Lui, 2001). Such acetaminophen assays are known to show interference. For instance, interference in the presence of elevated levels of bilirubin in biological samples producing erroneous results in such samples.

The present inventors postulated that the use of a strong oxidizing catalyst could be a contributing factor in the bilirubin interference that is seen with conventional acetaminophen assays. For instance, periodate has been used by certain reagent manufacturers to measure bilirubin by selective destruction of the bilirubin to form bilverdin. There is a significant change in absorbance as bilirubin is oxidized to bilverdin or higher oxidative products, which could contribute to the interference seen in conventional assays. Thus, the present inventors set out to determine if (a) a weak oxidizer could successfully drive an oxidative coupling reaction between a xylenol chromophore, such as 2,5-dimethylphenol, and p-aminophenol and (b) the use of a weak oxidizer would have a positive effect on bilirubin interference in the assay.

It has now surprisingly been demonstrated that the choice of a weak oxidizer, such as $MnCl_2$ as an exemplary catalyst having a low oxidative potential compared to sodium periodate or other strong oxidizers containing reactive oxygen species, provided sufficient energy to catalyze the coupling of p-aminophenol to 2,5-dimethylphenol in the reaction. Furthermore, it was successfully demonstrated that the choice of a weak oxidizer as the catalyst significantly reduced bilirubin interference in the assay, which is a highly desirable finding from a clinical perspective. It was further surprisingly discovered that a lower concentration of $MnCl_2$ was needed to drive the reaction compared to other catalysts tested and yet a stronger color development occurred in the assay. The use of less catalyst in the reagent reduces the chance of the catalyst reacting with other reagent components or with biological or chemical components present in the patient samples, thereby improving the assay.

The choice of a weak oxidizer as a catalyst may therefore reduce the potential for spontaneous oxidation of the xylenol chromophore and reactivity with other components present in the assay reagent over time, thereby improving reagent stability and extending the shelf-life of liquid-stable reagents. A skilled person will be able to distinguish a strong oxidizer from a weak oxidizer and will be able to select a suitable weak oxidizer for use as a catalyst in accordance with embodiments of the invention.

It was postulated that addition of an antioxidant to the chromophore reagent could further improve the color stability of the reagent over time. Surprisingly, it was demonstrated that addition of reduced glutathione, a component not commonly found in chromogenic assays, successfully prevented color development in the chromophore reagent over time, likely due in part to prevention of xylenol auto-oxidation, thereby improving reagent stability. Glutathione also functions as a scavenger and thus may remove radicals in the reagent that could potentially interfere in the oxidative coupling reaction.

Studies were conducted using hydroxylamine, 3,3'-thiodipropionic acid, thiourea or reduced glutathione. The reagents were monitored both qualitatively and quantitatively for color change over time. The addition of reduced glutathione to the reagent was the most effective in preventing color development over time.

Thus, R2 may optionally contain an anti-oxidant. Any suitable antioxidant may be utilized in accordance with the present invention. In one embodiment, R2 comprises an antioxidant in a concentration of about 0.005 g/L to about 5.00 g/L, or about 0.05 g/L to about 5 g/L, or about 0.1 g/L to about 1 g/L. In one embodiment, the antioxidant is glutathione. Reduced glutathione is particularly preferred. In one embodiment, R2 comprises reduced glutathione in a concentration of about 0.5 g/L.

R2 may optionally contain one or more of a buffer or a surfactant or a combination thereof. Any suitable buffer or surfactant may be utilized in accordance with the present invention, for example, those mentioned above with respect to the hydrolysis solution. The presence of a surfactant in the reagent may inhibit lipemic interference in the assay, particularly at low acetaminophen levels (i.e. <200 µmol/L).

In one embodiment, R2 comprises TRIS in a concentration of about 10 to 50 g/L or about 15 to 30 g/L or about 20 to 30 g/L. In one embodiment, R2 comprises about 24.2 g/L TRIS. In one embodiment, R2 comprises sodium carbonate in a concentration of about 5 to 20 g/L or about 10 to 15 g/L. In one embodiment, R2 comprises about 10.6 g/L sodium carbonate. In one embodiment, R2 comprises about 24.2 g/L TRIS and about 10.6 g/L sodium carbonate.

In some embodiments, the coupling reaction is carried out at about 37° C. with a basic pH between about 9 and 12, or between about 9.5 and 11.5, or preferably between about 10 and 11. In one embodiment, the pH is greater than about 10. In one embodiment, the pH is about 10.8.

The pH of the reagent may be adjusted by any suitable means known in the art. In one embodiment, NaOH pellets are added to R2 in a concentration of about 1 g/L to about 4 g/L or about 2 g/L to about 3 g/L. In one embodiment, R2 comprises about 2.5 g/L NaOH pellets.

An exemplary R2 formulation is shown in Table 2 below. In preparing R2 in accordance with this exemplary embodiment, it is recommended that the glutathione and 2,5-dimethylphenol be added last and in that order.

The pH of the assay reagent may be checked after preparation and can be further adjusted if needed.

The oxidative coupling reaction may take place at a temperature of about 10° C. to about 60° C., or about 30° C. to about 50° C., or about 35° C. to about 40° C. In one preferred embodiment, the oxidative coupling reaction takes place at a temperature of about 37° C.

The oxidative coupling reaction is allowed to proceed for a sufficient amount of time to permit coupling of the xylenol chromophore with substantially all of the p-aminophenol present in the reaction mixture, typically between about 2 to 20 minutes or between about 3 to 10 minutes. In one embodiment, the oxidative coupling reaction is continued for about 5 minutes. The length of the reaction can be optimized for the selected temperature since longer reaction times are generally needed for lower temperatures.

The oxidative coupling of the xylenol chromophore with p-aminophenol results in the formation of a blue product (i.e. a dye), which may be detected by measuring the change in absorbance of the assay mixture at an appropriate wavelength. The absorbance at the end of the hydrolysis reaction is subtracted from the absorbance at the end of the oxidative coupling reaction. The stoichiometric amount of acetaminophen present in the original sample is substantially equivalent to the stoichiometric amount of dye formed.

The absorbance of the resulting dye can be measured over a range of wavelengths. The maximum absorbance of the dye occurs at about 610-615 nm. Typically, the wavelength selected for measurement in a calorimetric assay is the wavelength at which peak absorbance occurs. If a bichromatic analyzer is utilized, a bichromatic blanking measurement is taken at an alternate wavelength, such as about 700 nm to about 850 nm, which is subtracted from the primary measurement to minimize background noise in the assay. Other known methods of minimizing background noise in an assay may also be used.

The present inventors surprisingly found that measuring the absorbance at an off-peak wavelength (i.e. on the shoulder of the absorbance curve rather than the peak) significantly decreased interference with the biological molecules bilirubin and hemoglobin in the assay. It was found that measuring absorbance at a wavelength of about 640 nm to about 680 nm, or about 650 nm to 670 nm, preferably about 660 nm, significantly improved acetaminophen measurement accuracy in the presence of bilirubin or hemoglobin. Bilirubin and hemoglobin interference are common disadvantages associated with known acetaminophen assays. Thus, to minimize interference with in the assay, the absorbance may be measured at about 660 nm.

In one embodiment, absorbance is measured between about 610 and 665 nm.

A skilled person will appreciate that while the components and their relative proportions in the reagent solutions can be varied without departing from the present invention, the presence of cloudiness, precipitates and other contaminating factors are to be avoided, both in the individual and combined solutions. Where the assay is a liquid-stable assay, any alterations that could negatively impact the stability of the reagents or the components thereof, such as enzyme or chromophore stability, should be assessed carefully.

In one exemplary embodiment, a two-part acetaminophen assay in accordance with the present invention is carried out as summarized briefly below.

The first part consists of the addition of an enzyme reagent (R1) to a patient serum or plasma sample at a certain sample to reagent ratio in a cuvette. On the Hitachi 717, for example, the sample volume is 10 µL and the R1 volume is 100 µL with a 100 µL on board dilution of R1 with de-ionized water to form a hydrolysis solution. The solution is allowed to incubate at 37° C. for set duration of time, such as 5 minutes, on the automated analyzer. During this time, the aryl acylamidase enzyme present in the reagent cleaves the amide bond of the acetaminophen molecule in the sample leaving p-aminophenol and acetate. Absorbance readings are monitored at an established wavelength and at certain time intervals prior to the introduction of a chromophore reagent.

In the second part, the chromophore reagent (R2) is introduced at a set time interval and a certain volume to the hydrolysis solution (sample+R1, diluted). On the Hitachi 717, for example, 200 µL of R2 is introduced and the reaction is monitored at set time intervals until completion of the time duration for the test. The xylenol chromophore in R2, preferably 2,5-dimethylphenol, oxidatively couples at an alkaline pH, in the presence of catalyst, with the p-aminophenol produced in the first part. In one preferred embodiment, the oxidative coupling step is carried out in the presence of manganese cations. The reaction produces a coloured complex that has a maximal absorption peak at about 610 nm.

The analyzer takes the difference between the absorbance prior to R2 addition and the absorbance at the end of the reaction, corrected for background noise. The difference in optical density is the amount of absorbance produced from that sample. The change in absorbance can be compared against a standard curve to calculate acetaminophen concentration in the original sample.

In a preferred embodiment, the absorbance is measured at 660 nm to minimize interference with certain biological molecules in the assay.

While not wishing to be bound by any particular theory, it is believed that the concentration of acetaminophen is directly proportional to the intensity of the absorbance according to the principle known as the Beer-Lambert Law, $A=\epsilon cl$, where:

$A$=absorbance (at a given wavelength);
$\epsilon$=molar extinction coefficient (a constant for every chemical);
$l$=length of the light path (i.e. 1 cm); and
$c$=concentration of the solute.

Therefore, the concentration of the solute (in this ease acetaminophen) is directly proportional to absorbance given that the molar extinction coefficient and the path length is constant.

In one embodiment, the concentrations in the final reaction mixture are:
1) 227.5 U/L Aryl Acylamidase
2) 0.0128 g/L $MnCl_2$
3) 3.66 g/L 2,5-dimethylphenol
4) 0.244 g/L Glutathione The assay of the present invention may be produced and sold as a kit of parts. The reagents in the kit may be powdered or lyophilized reagents requiring reconstitution. Methods of making such powdered or lyophilized reagents are know in the art. Preferably, the reagents are liquid-stable reagents. Liquid stable reagents are convenient to use and are less prone to errors that can be introduced during reconstitution.

In one embodiment, the kit comprises: a vessel comprising an enzyme reagent (R1); a vessel comprising a chromophore reagent (R2); and optionally directions for carrying out the assay. The kit may further comprise an acetaminophen standard and directions for preparing a linear set of standards.

EXAMPLES

Example 1

Exemplary Enzyme and Chromophore Reagents

TABLE 1

Exemplary enzyme reagent (R1) composition with deionized water as diluent.

| Ingredient | Amount/ L | Amount/ 100 µL | Conc. in Final Volume of 410 µL (10 µL sample + 100 µL R1 + 100 µL $H_2O$ + 200 µL R2) | Primary Purpose (may serve other functions as well) |
|---|---|---|---|---|
| CAPS | 6.460 g | 646 µg | 158 µg | Buffer |
| MnCl2•4H2O | 0.0525 g | 5.25 µg | 1.31 µg | Catalyst |
| BSA Fraction V | 1.000 g | 100 µg | 24.4 µg | Enzyme Stabilizer |
| Trehalose | 4.040 g | 404 µg | 98.9 µg | Enzyme |

TABLE 1-continued

Exemplary enzyme reagent (R1) composition with deionized water as diluent.

| Ingredient | Amount/ L | Amount/ 100 µL | Conc. in Final Volume of 410 µL (10 µL sample + 100 µL R1 + 100 µL H₂O + 200 µL R2) | Primary Purpose (may serve other functions as well) |
|---|---|---|---|---|
| Gentamycin Sulfate | 0.010 g | 1.0 µg | 2.44 µg | Stabilizer Preservative |
| Sodium p-Hydroxy-benzoate | 1.000 g | 100 µg | 24.4 µg | Enzyme Stabilizer |
| EDTA | 0.025 g | 2.5 µg | 0.61 µg | Metal Chelator |
| PVP-40 | 2.000 g | 200 µg | 48.8 µg | Protein Stabilizer |
| 2N NaOH | 833 µL | 0.083 µL | 0.02 µL | pH adjuster |
| Sodium Azide | 0.050 g | 5.0 µg | 1.2 µg | Preservative |
| Aryl Acylamidase | 932.7 U | 0.093 U | 0.023 U | Enzyme |

TABLE 2

Exemplary chromophore reagent (R2) composition with deionized water as diluent.

| Ingredient | Amount/ L | Amount/ 200µL | Conc. in Final Volume of 410 µL (101 µL sample + 100 µL R1 + 100 µL H2O +200 µL R2) | Primary Purpose (may serve other functions as well) |
|---|---|---|---|---|
| TRIS | 24.200 g | 4.840 mg | 2.360 mg | Buffer |
| Sodium Carbonate | 10.608 g | 2.121 mg | 1.061 mg | Buffer |
| NaOH Pellets | 2.500 g | 500 µg | 244 µg | Buffer |
| Glutathione | 0.500 g | 100 µg | 48.8 µg | Anti-oxidant |
| 2,5-Dimethylphenol | 7.500 g | 1.5 mg | 732 µg | Chromophore |

The reagents may be prepared in a suitable diluent, such as deionized water.

Example 2

Performance of Assay in Absence and Presence of NAC

A set of standards was prepared having a known concentration of acetaminophen in deionized water (i.e. 250 µmol/L, 1000 µmol/L, 1500 µmol/L, 2000 µmol/L, and 2500 µmol/L). A 10 µL aliquot of each standard was added to 100 µL of R1 in a cuvette in a Hitachi 717® Analyzer (Roche Diagnostics) followed by an on board dilution with 100 µl deionized water. Each mixture was allowed to incubate at 37° C. for 5 minutes. An initial absorbance value was obtained for each. A 200 µL aliquot of R2 was added to each cuvette. The oxidative-coupling reaction was allowed to proceed for 5 minutes. A final absorbance value was obtained. The concentration of acetaminophen was calculated based on the difference in absorbance at 660 nm between the final and initial absorbance, corrected for background noise by subtracting the absorbance at 800 nm. The results for various known concentrations are shown in Table 3 below.

TABLE 3

Measured acetaminophen concentration in the absence of NAC using p-xylenol as chromophore.

| [Acetaminophen] in sample (µmol/L) | Measured [Acetaminophen] (µmol/L) | % Difference |
|---|---|---|
| 250 | 248 | −0.8 |
| 500 | 496 | −0.8 |
| 1000 | 995 | −0.5 |
| 1500 | 1498 | −0.1 |
| 2000 | 1987 | −0.7 |
| 2500 | 2479 | −0.8 |

The assay demonstrated accurate measurement of acetaminophen concentration across a wide range of acetaminophen concentrations.

To assess performance in the presence of NAC, a stock solution was made by dissolving 75 mg of NAC into 1000 µL of deionized water. This produced a 75 g/L or 75000 mg/L NAC concentrated stock solution.

A 2.5 ml aliquot of a known concentration of acetaminophen in water was added to a test tube and this was spiked with 50 µL of the NAC stock solution to prepare a set of spiked standards having a known concentration of acetaminophen (i.e. 245 µmol/L, 490 µmol/L, 980 µmol/L, 1470 µmol/L, 1960 µmol/L, and 2450 µmol/L). Each spiked acetaminophen standard had a NAC concentration of 1471 mg/L, which is a value that could be found in patient serum during NAC treatment. Samples were analyzed within an hour of spiking since NAC degrades over time.

The assay was carried out as described above. A 10 µL aliquot of spiked standard was added to 100 µL of R1 in a cuvette in a Hitachi 717® followed by an on board dilution. Each mixture was allowed to incubate at 37° C. for 5 minutes. An initial absorbance value was obtained. A 200 µL aliquot of R2 was added to the respective cuvettes. The oxidative-coupling reaction was allowed to proceed for 5 minutes. Based on the difference in absorbance at 660 nm, corrected for background, the concentrations of acetaminophen were calculated. Method comparison was done on the Siemens Advia® 1650 to compare a known assay using an 8-HQ derivative as the chromophore. The results for various known concentrations of acetaminophen are shown in Table 4 below.

TABLE 4

Measured acetaminophen concentration in the presence of NAC using 8-HQ5SA or p-xylenol as chromophore.

| [Acetaminophen] in spiked samples (µmol/L) | Measured [Acetaminophen] (µmol/L) | | % Difference from Theoretical | |
|---|---|---|---|---|
| | 8-HQ derivative | p-xylenol | 8-HQ derivative | p-xylenol |
| 245 | 104 | 257 | −57.55 | 4.90 |
| 490 | 219 | 505 | −55.31 | 3.06 |
| 980 | 478 | 1009 | −51.22 | 2.96 |
| 1470 | 718 | 1506 | −51.16 | 2.45 |
| 1960 | 1019 | 1993 | −48.01 | 1.68 |
| 2450 | 1302 | 2481 | −46.86 | 1.27 |

The assay with p-xylenol as the chromophore was resistant to interference in the presence of NAC compared to an assay using an 8-HQ derivative as the chromophore. The cut off for interference in a clinical assay is generally a 10% difference, preferably less than 5%.

Example 3

Comparison of Xylenol Chromophores

Comparison of the xylenol chromophores was conducting by substituting the chromophore in the R2 formulation. All other parameters were the same. A stock solution of the R2 buffer and glutathione was made and then split into six batches. 7.5 g/L, of each respective isomer was dissolved in each respective batch, thereby creating six "different" chromophore reagents with a different isomer in each, R1 was kept constant therefore the only variable in the analysis was the chromophore in R2, The enzyme reagent (R1) had a pH of 8.6 @ 25° C., while the six isomeric xylenol reagents each had a pH of 11.5@ 25° C. The results of the various known isomers are shown in Table 5 below.

The results demonstrated that 2,5-dimethylphenol, 2,6-dimethylphenol, and 2,3-dimethylphenol produced acceptable linearity results in the presence of NAC. The best performance was seen with 2,5-dimethylphenol and 2,6-dimethylphenol.

TABLE 5

Acetaminophen concentration measured using different xylenol chromophores in the presence and absence of NAC.

| | Dimethylphenol | | | | | |
|---|---|---|---|---|---|---|
| | 2.5 | 3.4 | 2.6 | 2.4 | 3.5 | 2.3 |
| [Acetaminophen] (μmol/L) No NAC | | | | | | |
| 250 | 252 | 89 | 251 | 224 | 234 | 254 |
| 500 | 502 | 273 | 502 | 488 | 476 | 502 |
| 1000 | 1000 | 982 | 999 | 998 | 998 | 1000 |
| 1500 | 1499 | 2180 | 1505 | 1519 | 1561 | 1487 |
| 2000 | 1991 | 3577 | 1998 | 2034 | 2138 | 1954 |
| 2500 | 2483 | 5014 | 2483 | 2533 | 2753 | 2426 |
| [Acetaminophen] (μmol/L) NAC (1471 mg/L) Spiked Set | | | | | | |
| 245 | 255 | 34 | 248 | 56 | 138 | 247 |
| 490 | 505 | 78 | 491 | 141 | 292 | 488 |
| 980 | 999 | 188 | 985 | 314 | 606 | 961 |
| 1470 | 1481 | 337 | 1478 | 556 | 945 | 1413 |
| 1960 | 1947 | 518 | 1959 | 828 | 1318 | 1861 |
| 2450 | 2401 | 738 | 2440 | 1108 | 1706 | 2304 |

Example 4

Evaluation of 2,5-dimethylphenol in the Presence of Intralipid®

An evaluation of 2,5-dimethylphenol was carried out using Intralipid®-spiked serum containing a known concentration of acetaminophen. It was shown that, at a therapeutic level of acetaminophen (<200 μmol/L), the 2,5-dimethylphenol chromophore recovered within the acceptable limit of ±10% at 200 mg/dL Intralipid®. Testing was carried out on the Siemens Advia® 1650.

First, 10 ml of serum was pooled into a large test tube and mixed. The serum was then spiked with 2.1 mg of reagent grade acetaminophen and mixed until dissolved. From the spiked pool, one 4.75 ml aliquot was pipetted out and placed in a large test tube marked as control pool. A second aliquot of 4.75 ml was pipetted out and placed in a second large test tube marked as test pool. In the control pool, 250 μL of saline was added to the pool and mixed thoroughly. In the test pool, 250 μL of 20% Intralipid® solution was added and mixed thoroughly. An interference set was made by mixing the control and test pools at varying levels, thereby creating different Intralipid® concentrations but maintaining the acetaminophen concentration. The 2,5-dimethylphenol demonstrated acceptable results to at least 200 mg/dL Intralipid®.

Example 5

Performance of Different Chromophores in the Presence of NAC

Known acetaminophen assays using 8-hydroxyquinoline or a derivative thereof as a chromophore are subject to interference in the presence of therapeutic levels of NAC (i.e. >800 mg/L). The present inventors tested two commercially available acetaminophen assays (Genzyme Diagnostics Inc., PEI, Canada) containing either 8-hydroxyquinoline-5-sulfonic acid (8-HQ5SA) or 8-hydroxyquinoline hemisulfate (8-HQHS) as the chromophore. While all provided accurate acetaminophen measurements in the absence of NAC, they all showed a significant (i.e. >10%) decrease in acetaminophen recovery in the presence of therapeutic levels of NAC. It was discovered that the presence of NAC affected the oxidative coupling reaction in the assay rather than the enzymatic conversion of acetaminophen to p-aminophenol. There was a considerable difference in recovery between the 8-HQ5SA assay and the 8-HQHS assay, with the 8-HQ5SA assay being more susceptible to NAC interference, suggesting that even a slight difference in the chemical structure of the chromophore can be crucial to the coupling reaction when NAC is present.

A comparison of p-xylenol and 8-hydroxyquinoline-5-sulfonic acid (8HQ5SA) was conducted by replacing the 8HQ5SA in a commercial kit (Genzyme Diagnostics P.E.I. Inc., PEI, Canada) with p-xylenol. All other parameters of the reagents and assays were the same. A manual assay using a 1000 μmol/L acetaminophen standard was carried out. The control was spiked with water and the test sample was spiked with 1000 mg/L NAC. The absorbance was measured across a spectrum of wavelengths.

Figure 2:
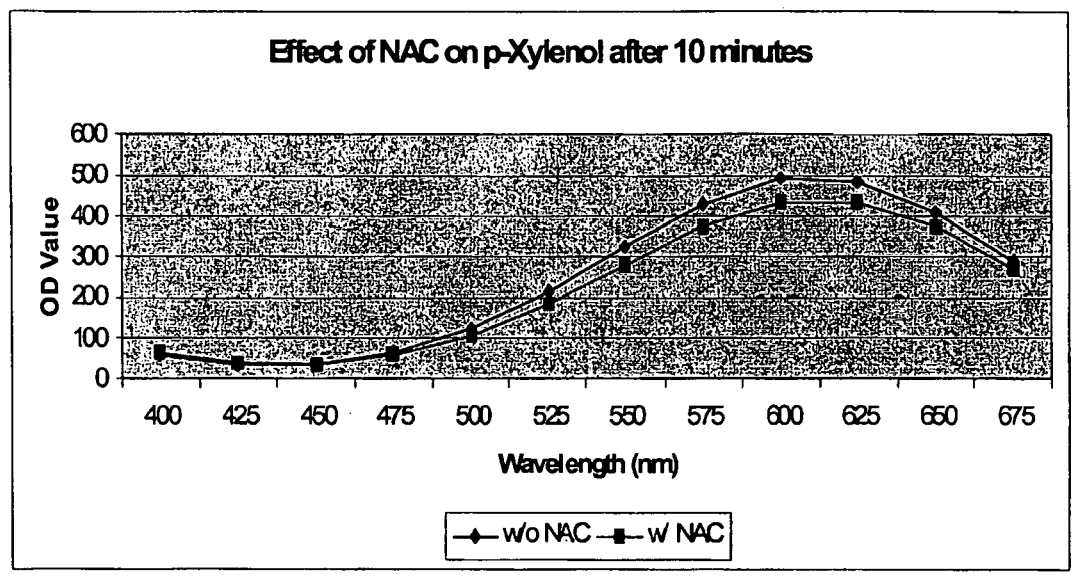
FIG. 2 shows the results of an acetaminophen assay carried out as above in FIG. 1 with the only difference being that 8-HQ5SA is replaced with p-xylenol as the chromophore, wherein the results demonstrate that p-xylenol is relatively unaffected by the presence of therapeutic levels of NAC.

FIG. 1 shows the results for the assay carried out with 8HQ5SA as the chromophore and FIG. 2 shows the results for p-xylenol. The results indicate that the p-xylenol assay was relatively unaffected by the presence of NAC, demonstrating a robust assay, whereas the assay with 8HQ5SA was significantly affected by the presence of NAC.

Example 6

Parameter Modifications Reduce Hemoglobin and Bilirubin Interference

Hemoglobin interference is a disadvantage of known acetaminophen assays. An Ultrospec™ 3300 scan of a 100 μmol/L acetaminophen sample spiked with 1000 mg/dL of hemoglobin was carried out and produced an interesting observation, The OD shift between a 100 μmol/L acetaminophen sample and the 100 μmol/L+1000 mg/dL Hemoglobin sample was much greater at 600 nm than at 660 nm, which was on the shoulder of the absorbance peak yet still provided a good OD shift between the primary and secondary wavelengths. Therefore further testing was conducted using 660 nm as the primary wavelength and keeping 800 nm as the secondary wavelength.

The results demonstrated that changing the primary wavelength from 600 nm to 660 nm significantly reduced interference in the presence of both hemoglobin and bilirubin in the assay. Analysis was carried out on both the Hitachi 717 and the Siemens Advia® 1650. Serum was spiked with acetaminophen at a set concentration and then with the interfering material at varying concentrations. The modified assay showed acceptable levels of interference (i.e. <10%) in the presence of NAC, bilirubin and hemoglobin.

Example 7

Effect of Chromophore on Bilirubin Interference

A bilirubin interference study was conducted in which all reagents used in the acetaminophen assay were identical with the exception of the chromophore. Samples assayed contained about 100 μmol/L or 330 μmol/L acetaminophen. The chromophores analyzed were 8-HQ5SA and p-xylenol. The reactions were analyzed on a Siemens Advia® 1650.

TABLE 6

Bilirubin interference at about 100 pmol/L acetaminophen.

| | 8-HQ derivative | | p-xylenol | |
|---|---|---|---|---|
| Bilirubin Conc. (mg/dL) | Acetaminophen Conc. Measured (μmol/L) | Difference from Control Value (μmol/L) | Acetaminophen Conc. Measured (μmol/L) | Difference from Control Value (μmol/L) |
| 0 | 102 (control) | (set) | 105 (control) | (set) |
| 4 | 117 | 15 | 97 | −8 |
| 8 | 131 | 29 | 98 | −7 |
| 16 | 158 | 56 | 102 | −3 |
| 24 | 186 | 84 | 103 | −2 |
| 32 | 212 | 110 | 104 | −1 |
| 40 | 237 | 135 | 104 | −1 |

TABLE 7

Bilirubin interference at about 330 jmol/L acetaminophen.

| | 8-HQ derivative | | p-xylenol | |
|---|---|---|---|---|
| Bilirubin Conc. (mg/dL) | Acetaminophen Conc. Measured (μmol/L) | Difference from Control Value (μmol/L) | Acetaminophen Conc. Measured (μmol/L) | Difference from Control Value (μmol/L) |
| 0 | 316 (control) | (set) | 324 (control) | (set) |
| 4 | 330 | 14 | 318 | −6 |
| 8 | 341 | 25 | 320 | −4 |
| 16 | 368 | 52 | 322 | −2 |
| 24 | 392 | 76 | 324 | 0 |
| 32 | 415 | 99 | 324 | 0 |
| 40 | 438 | 122 | 326 | 2 |

The results demonstrate that the choice of chromophore can significantly impact bilirubin interference in the assay. The assay using p-xylenol was significantly more resistant to bilirubin interference.

The above-described embodiments of the invention are intended to be examples only. Alterations, modifications and variations can be effected to the particular embodiments by those of skill in the art without departing from the scope of the invention, which is defined solely by the claims appended hereto.

All references cited are incorporated herein by reference in their entirety.

What is claimed is:

1. A method for determining the concentration of acetaminophen in an aqueous sample, the method comprising the steps of:
hydrolyzing acetaminophen to form p-aminophenol;
oxidatively coupling said p-aminophenol to a xylenol chromophore in the presence of a suitable catalyst to form a colored product; and
determining the amount of said colored product formed, the amount of said colored product formed being proportional to the amount of acetaminophen present in said aqueous sample,
wherein the method is reliable in the presence or absence of therapeutic levels of N-acetylcysteine (NAC) in said aqueous sample.

2. The method of claim 1, wherein the step of hydrolyzing acetaminophen to p-aminophenol comprises contacting the acetaminophen with an aryl acylamidase.

3. The method of claim 2, wherein said xylenol chromophore is selected from the group consisting of 2,5-dimethylphenol, 2,6-dimethylphenol and 2,3-dimethylphenol.

4. The method of claim 3, wherein said catalyst is a weak oxidizer.

5. The method of claim 4, wherein said xylenol chromophore is 2,5-dimethylphenol and said catalyst is anhydrous or hydrated $MnCl_2$.

6. The method of claim 5, wherein the aqueous sample is serum or plasma.

7. An assay for determining the concentration of acetaminophen in an aqueous sample, the assay comprising the steps of
contacting the aqueous sample with a first reagent (R1) comprising an aryl acylamidase enzyme and a suitable diluent to form a hydrolysis solution;
optionally, diluting the hydrolysis solution;
incubating the hydrolysis solution to permit a hydrolysis reaction wherein the acetaminophen is converted to p-aminophenol;
contacting the hydrolysis solution with a second reagent (R2) comprising a xylenol chromophore and a suitable diluent, to form an oxidative coupling solution;
incubating the oxidative coupling solution to permit an oxidative coupling reaction wherein the xylenol chromophore is coupled to the p-aminophenol in the presence of a suitable catalyst to form a colored product; and
determining the amount of the colored product formed, the amount of the colored product formed being proportional to the amount of acetaminophen present in the aqueous sample,
wherein the assay is reliable in the presence or absence of therapeutic levels of N-acetylcysteine (NAC) in the aqueous sample.

8. The assay of claim 7, wherein R1 comprises aryl acylamidase at a concentration of about 10 U/L to about 5000 U/L.

9. The assay of claim 8, wherein the xylenol chromophore is selected from the group consisting of 2,5-dimethylphenol, 2,6-dimethylphenol and 2,3-dimethylphenol.

10. The assay of claim 9, wherein the catalyst is a weak oxidizing catalyst and wherein the catalyst is present in R1 in a concentration of about 0.0005 g/L to about 1.000 g/L.

11. The assay of claim 10, wherein R2 comprises 2,5-dimethylphenol in a concentration of about 0.075 g/L to about 115 g/L and/or wherein the catalyst is $MnCl_2.4H_2O$ and is present in R1 in a concentration of about 2.5 g/L to about 20 g/L.

12. The assay of claim 11, wherein R2 further comprises reduced glutathione in a concentration of about 0.005 g/L to about 5.000 g/L.

13. The assay of claim 12, wherein R1 further comprises one or more of a protein solubilizer, a protein stabilizer, an enzyme stabilizer, a metal chelator, a buffer, a surfactant, a pH adjuster, a preservative, or an excipient.

14. The assay of claim 13, wherein the enzyme stabilizer is selected from the group consisting of PVP-40, BSA Fraction V, trehalose, sodium p-hydroxybenzoate, p-hydroxybenzoic acid and combinations thereof.

15. The assay of claim 14, wherein R2 further comprises one or more of a buffer, a surfactant, a pH adjuster, a preservative, an antioxidant or an excipient.

16. The assay of claim 15, wherein the diluent is deionized water and the hydrolysis solution is diluted approximately 1:1 with the diluent prior to the hydrolysis reaction.

17. The assay of claim 16, wherein R1 comprises about 932.7 U/L aryl acylamidase and about 0.0525 g/L $MnCl_2.4H_2O$; and wherein R2 comprises about 7.5 g/L 2,5-dimethylphenol and about 0.500 g/L reduced glutathione.

18. The assay of claim 10, wherein the hydrolysis reaction and the oxidative coupling reaction each take place at a temperature of about 37° C. for about 3 to 10 minutes, and wherein the hydrolysis reaction takes place at a pH of about 8.6 and the oxidative coupling reaction takes place at a pH of about 10.8.

19. The assay of claim 18, wherein the concentration of acetaminophen is determined by obtaining the difference in absorbance at the end of the hydrolysis reaction and at the end of the oxidative coupling reaction; and comparing the difference against a standard or set of standards, wherein the absorbance is measured at a wavelength between about 610 nm and 665 nm.

20. The assay of claim 19, wherein the absorbance is measured at a wavelength of about 660 nm.

21. The assay of claim 10, wherein the aqueous sample is serum or plasma.

22. A method for determining the concentration of p-aminophenol in an aqueous sample, the method comprising the steps of oxidatively coupling the p-aminophenol to a xylenol chromophore selected from the group consisting of 2,5-dimethylphenol, 2,6-dimethylphenol and 2,3-dimethylphenol, in the presence of a catalyst to form a colored product, the catalyst being a weak oxidizer; and determining the amount of the colored product formed, the amount of the colored product formed being proportional to the amount of p-aminophenol initially present in the aqueous sample.

23. The method of claim 22, wherein the catalyst is hydrated $MnCl_2$ and
the xylenol chromophore is 2,5-dimethylphenol.

* * * * *